(12) United States Patent
Minassians

(10) Patent No.: US 7,875,021 B2
(45) Date of Patent: Jan. 25, 2011

(54) CLOSED SPECIMEN COLLECTION SYSTEM

(76) Inventor: Nastaran Minassians, 325 E. Santa Anita Ave., #217, Burbank, CA (US) 91502

(*) Notice: Subject to any disclaimer, the term of this patent is extended or adjusted under 35 U.S.C. 154(b) by 673 days.

(21) Appl. No.: 11/858,073

(22) Filed: Sep. 19, 2007

(65) Prior Publication Data
US 2009/0076471 A1  Mar. 19, 2009

(51) Int. Cl.
*A61M 27/00* (2006.01)
*A61M 25/00* (2006.01)
*A61M 25/16* (2006.01)
*A61M 25/18* (2006.01)
*A61M 39/00* (2006.01)
*A61M 39/10* (2006.01)

(52) U.S. Cl. .............. 604/544; 604/517; 604/523; 604/533; 128/207.14; 128/207.16

(58) Field of Classification Search .............. 604/322, 604/403, 540, 517, 523, 533–535, 544
See application file for complete search history.

(56) References Cited

U.S. PATENT DOCUMENTS

| | | | |
|---|---|---|---|
| 3,579,303 A | 5/1971 | Pickering | |
| 4,062,363 A | 12/1977 | Bonner, Jr. | |
| 4,068,659 A | 1/1978 | Moorehead | |
| 4,190,059 A | 2/1980 | Holt | |
| 4,327,723 A | 5/1982 | Frankhouser | |
| 4,515,592 A * | 5/1985 | Frankhouser | 604/163 |
| 4,617,941 A * | 10/1986 | Ichikawa et al. | 600/578 |
| 4,702,740 A | 10/1987 | Bates | |
| 4,753,638 A | 6/1988 | Peters | |
| 4,932,938 A | 6/1990 | Goldberg et al. | |
| 4,941,580 A * | 7/1990 | Julian | 215/235 |
| 4,972,844 A | 11/1990 | Cianci et al. | |
| 5,096,454 A | 3/1992 | Samples | |
| 5,108,927 A | 4/1992 | Dorn | |
| 5,140,999 A | 8/1992 | Ardito | |
| 5,176,665 A | 1/1993 | Watanabe et al. | |
| 5,365,960 A | 11/1994 | Bran | |
| 5,409,459 A | 4/1995 | Gambale | |
| 5,501,669 A | 3/1996 | Conway et al. | |
| 5,511,557 A | 4/1996 | Hazard et al. | |
| 5,637,091 A | 6/1997 | Hakky et al. | |
| 5,782,808 A * | 7/1998 | Folden | 604/265 |
| 5,785,694 A | 7/1998 | Cohen et al. | |
| 5,979,475 A | 11/1999 | Satoh et al. | |

(Continued)

*Primary Examiner*—Melanie J Hand
(74) *Attorney, Agent, or Firm*—David A. Belasco; Belasco Jacobs & Townsley, LLP

(57) ABSTRACT

A closed specimen collection system includes a port tube that is rotatably attached to tubing of a urinary drainage system attached to an indwelling urinary catheter. The port tube has a one-way valve located adjacent one end formed to fit sealably with a shaped nozzle. A collection has a proximal end and a distal end with a shaped nozzle at the proximal end adapted to fit sealably into the port tube adjacent the one-way valve. A specimen container has a hollow body, a back end and a front end with a sealable aperture sized and shaped to attach to the distal end of the collection tube. A piston fits closely within the hollow body and is attached to an actuating rod. When the actuating rod is moved away from the front end of the container, urine will flow into the specimen container through the collection tube in a sterile condition.

15 Claims, 3 Drawing Sheets

U.S. PATENT DOCUMENTS

| | | |
|---|---|---|
| 5,993,436 A | 11/1999 | Kitou et al. |
| 6,045,542 A | 4/2000 | Cawood |
| 6,235,010 B1 | 5/2001 | Wilkinson et al. |
| 6,440,119 B1 | 8/2002 | Nakada et al. |
| 6,588,427 B1 * | 7/2003 | Carlsen et al. ......... 128/207.14 |
| 6,732,875 B2 | 5/2004 | Smith et al. |
| 6,743,198 B1 | 6/2004 | Tihon |
| 6,783,522 B2 | 8/2004 | Fischell |
| 6,793,651 B1 * | 9/2004 | Bennett et al. .............. 604/544 |
| 6,827,705 B2 | 12/2004 | Bierman |
| 6,830,563 B1 | 12/2004 | Singer |
| 6,913,244 B1 | 7/2005 | Atkinson et al. |
| 7,150,740 B2 | 12/2006 | Bennett et al. |
| 2004/0181192 A1 * | 9/2004 | Cuppy ........................ 604/256 |

* cited by examiner

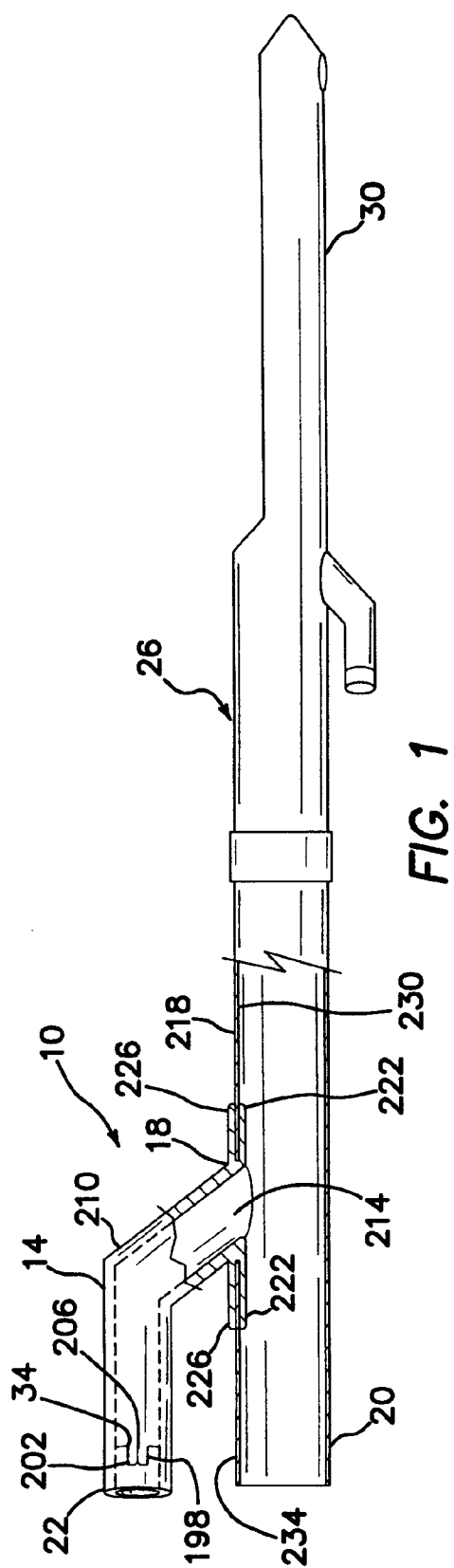
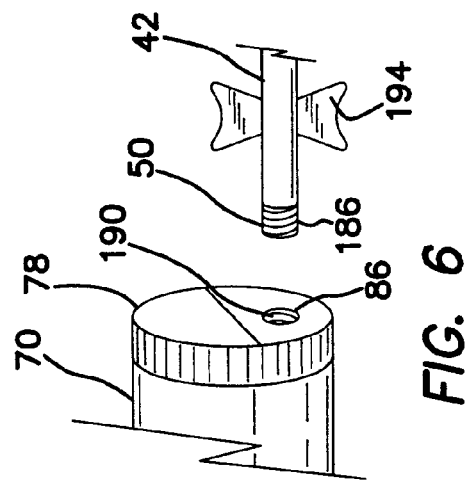
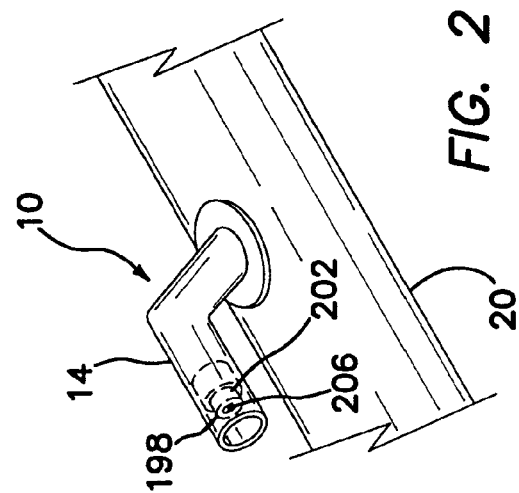

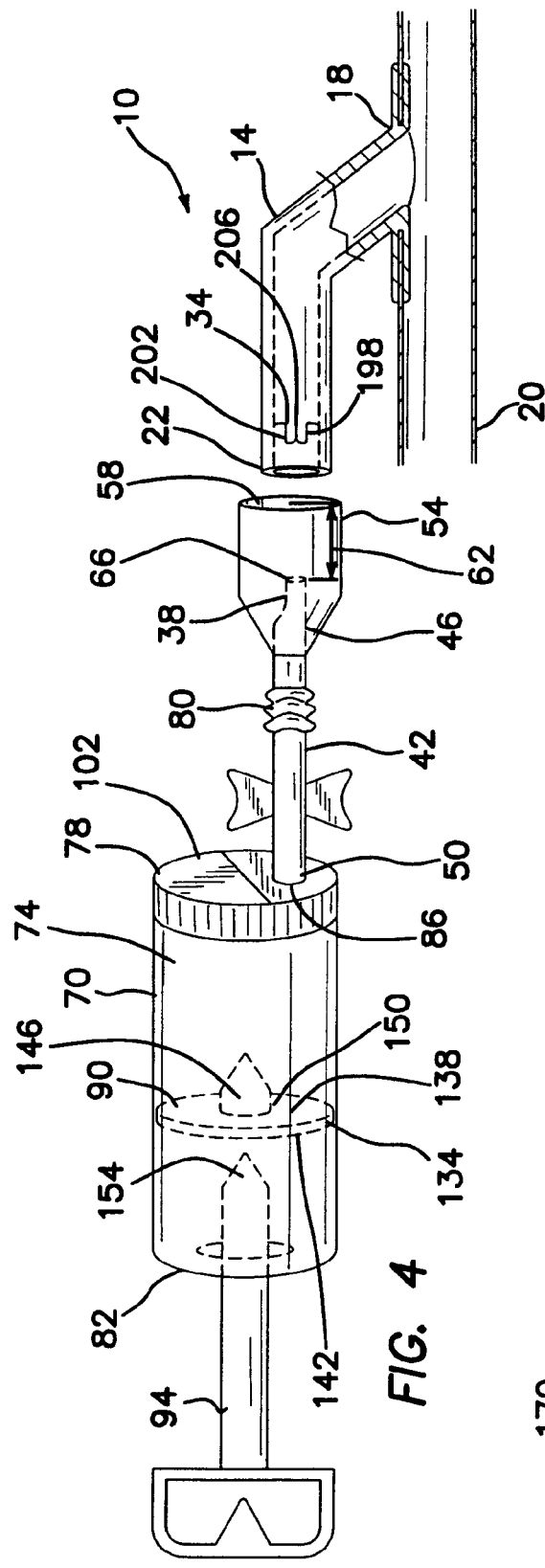
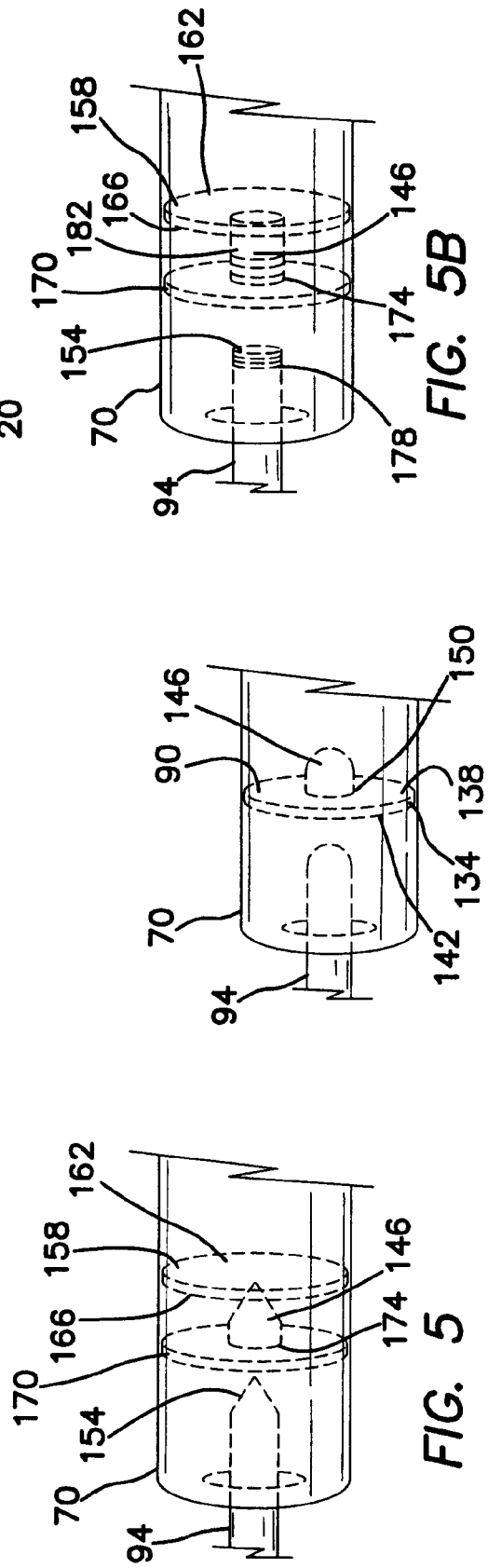

CLOSED SPECIMEN COLLECTION SYSTEM

FIELD OF INVENTION

This invention relates to the field of fluid specimen collection, and more specifically to a system for obtaining sterile urine specimens without the use of aspirating needles.

BACKGROUND OF THE INVENTION

Health care providers are frequently required to obtain urine specimens from patients for laboratory testing. In hospital environments, patients are often catheterized when their conditions require them to be bedridden. While present systems allow for nurses and other health care workers to obtain urine specimens from the patient's indwelling catheter, such systems require the use of syringes and are difficult and potentially dangerous, both to the health care provider and to the patient. The dangers arise from the use of syringes, which can result in accidental needle sticks, and from infections introduced through non-sterile interfaces for obtaining the specimens. The present systems use a rubber membrane on a fixed port of tubing attached to the catheter. This membrane is penetrated with a syringe which is used to withdraw the specimen. The rubber membrane may become contaminated and thereby compromise the specimen or infect the patient. The present invention seeks to eliminate these problems and provide a system that is both safer an easier to use.

U.S. Pat. No. 6,793,651, issued to Bennett et al., discloses a urinary catheter system that includes a urinary catheter, a connector and a medical implement which is readily attached to or removed from the connector. When a medical implement such as a collection appliance is attached to the connector, fluid such as urine can flow from the patent and into the collection appliance. Alternatively, when a syringe is attached to the connector, the catheter system may be irrigated to remove debris and other foreign matter, or the syringe may be used to provide medication to the patient. The system is preferably a closed system in which the connector includes a resealable valve which prevents the flow of fluid through the connector if a medical implement is not attached.

U.S. Pat. No. 6,045,542, issued to Cawood is directed to a flat urinary drainage bag that can be worn by a patient over the abdomen with the bag suspended from a waist-encircling belt is disclosed. The device includes an inlet tube for connection to a urethral catheter and a valve-equipped drain tube that extends downwardly from the bag when the drain tube is used to drain the contents there from. The lower end of the bag is foldable upwardly to position the drain tube in an upwardly-facing raised position against the bag's front wall, and a retaining strap is located across the front wall for holding the drain tube in its raised position. Spot attachments that secure the ends of the strap to the bag's front wall also secure the front and rear walls of the bag together, thereby performing multiple functions of limiting bulging of the bag in use, reducing sloshing of the bag's contents, and securing the retaining strap (and the raised drainage tube) in place.

U.S. Pat. No. 5,176,665, issued to Watanabe et al. discloses an antimicrobial device adapted for passage through the drainage port of a urinary drainage container. This invention concerns also a patient-care system comprising, in combination, a urinary drainage container comprising a drainage port for inserting an antimicrobial device into the container, and an antimicrobial delivery device. The antimicrobial device delivers an agent into the container for preventing and eliminating unwanted pathogens inside the container. The invention relates also to a method for preventing and eliminating unwanted pathogens in a urine receiving container by inserting through the drainage exit into the container, a device for delivering an antimicrobial agent in the container.

U.S. Pat. No. 4,723,950, issued to Lee discloses a urine drainage bag having an outlet tube housing a microcidal tube is disclosed. The microcidal tube is manufactured from polymeric materials capable of absorbing and releasing antimicrobial substances in a controllable sustained time release mechanism, activated upon contact with droplets of urine, thereby preventing the retrograde migration of infectious organisms into the drainage bag.

U.S. Pat. No. 4,784,654, issued to Beecher is directed to an improved female urinary appliance is disclosed. The appliance includes a mouth surrounding a urine-receiving cavity, and a drainage channel. The mouth is adapted to be positioned within the labia folds of the user, in contact with the vestibular tissue around the meatus and held in place by gentle vacuum. A valve is preferably used in combination with the appliance, and includes an inlet and an outlet, for maintaining a pre-selected vacuum condition at the valve inlet and a predetermined pressure condition at the valve outlet is disclosed. In preferred use, the drainage channel is suitable connected in spaced relation to the valve inlet. The valve contains a flow control element adapted to control flow of urine from the cavity. While the mouth is held against the vestibular tissue by gentle vacuum, urine flowing through the appliance and valve entrains gas present in the cavity. In the cavity, a desired vacuum condition is maintained, over time, because the valve includes a semi-permeable membrane adapted to permit air and other gas to diffuse through a portion of the valve and thereby to counteract the effects of entrainment and relieve or maintain the vacuum condition at a predetermined level.

U.S. Pat. No. 4,702,740, issued to Bates discloses a collection system for body fluids comprising, a receptacle having a collection chamber for retaining the body fluids, a first container having a supply chamber for retaining a bactericide, and a second container having a holding chamber, with the holding chamber being located above a lower portion of the collection chamber, and the supply chamber being located above a lower portion of the holding chamber. The system has a first valve member permitting the passage of bactericide from the supply chamber into the holding chamber, and a second valve member permitting the passage of the bactericide from the holding chamber into the collection chamber.

It is an objective of the present invention to provide a system for collection of urine from patients with indwelling catheters that will prevent the contamination of the urine so that it can be used for laboratory procedures. It is a further objective to provide such a system that will prevent infection of the patient due to procedures used for obtaining the samples. It is a still further objective of the invention to provide the above features without the use of syringes. It is yet a further objective to provide a system that is easy for hospital personnel to use. Finally, it is an objective of the present invention to provide such a system that is reliable, inexpensive to produce and disposable.

While some of the objectives of the present invention are disclosed in the prior art, none of the inventions found include all of the requirements identified.

SUMMARY OF THE INVENTION

The present invention addresses all of the deficiencies of prior art closed specimen collection system inventions and satisfies all of the objectives described above.

(1) A closed specimen collection system providing the desired features may be constructed from the following components. A port tube is provided. The port tube has a first end, a second end and is rotatably attached at the first end to tubing of a urinary drainage system attached to an indwelling urinary catheter. The port tube has a one-way valve located adjacent the second end. The second end is formed to fit sealably with a shaped nozzle.

(2) In a variant of the invention, a collection tube is provided. The collection tube has a proximal end and a distal end and has a shaped nozzle at the proximal end. The shaped nozzle is adapted to fit sealably into the port tube at the second end adjacent the one-way valve. A protective cover is provided. The cover is attached to the collection tube adjacent the proximal end, has a hollow interior and extends a first predetermined distance past an outer end of the shaped nozzle. A specimen container is provided. The container has a hollow body, a front end and a back end. The front end has an aperture. The aperture is sized and shaped to attach to the distal end of the collection tube. The aperture is sealable after removal of the distal end of the collection tube there from. A piston is provided. The piston fits closely within the hollow body and is attached to an actuating rod. When the port tube is connected to the collection tube, the collection tube is connected to the specimen container and the actuating rod is moved away from the front end of the container, urine will flow into the specimen container in a sterile condition.

(3) In another variant, the collection tube further includes a flexible portion between the proximal end and the distal end.

(4) In still another variant, the front end of the specimen container includes a rotating lid, the lid sealably closing the aperture.

(5) In yet another variant, a latching mechanism is provided. The latching mechanism controls rotation of the lid.

(6) In a further variant, the latching mechanism further includes a rotating portion. The rotating portion is affixed to a leading edge of the rotating lid and has a projecting ledge located parallel to the leading edge. A fixed portion is provided. The fixed portion is attached to the front end of the specimen container and has a receiving slot sized, shaped and located to mate frictionally with the projecting ledge. When the rotating lid is positioned to seal the aperture, the projecting ledge will be secured within the receiving slot.

(7) In still a further variant, the latching mechanism further includes a retracting tab attached to the rotating portion, the retracting tab assisting in opening the aperture.

(8) In yet a further variant, the piston further includes a seal. The seal has a front side and a back side and is sized and shaped to fit closely within the hollow body. The seal is located adjacent the front end of the specimen container. The seal has a central receiving port located at its center portion. A first end of the actuating rod is sized and shaped to removably engage the central receiving port. When the actuating rod has withdrawn the piston toward the back end of the specimen container, the actuating rod is removed from the receiving port, the aperture is sealed and the specimen container will contain a sterile urine sample.

(9) In another variant of the invention, the piston further includes a first seal. The first seal has a front side and a back side and is sized and shaped to fit closely within the hollow body. The first seal is located adjacent the front end of the specimen container. A second seal is provided. The second seal is sized and shaped to fit closely within the hollow body and has a central receiving port located at a center portion of the second seal. The second seal is spaced from the back side of the first seal and attached thereto at an outer surface of the receiving port. A first end of the actuating rod is sized and shaped to removably engage the central receiving port. When the actuating rod has withdrawn the piston toward the back end of the specimen container, the actuating rod is removed from the receiving port, the aperture is sealed and the specimen container will contain a sterile urine sample.

(10) In still another variant, the actuating rod has a male thread at the first end and the central receiving port has a mating female thread.

(11) In yet another variant, the distal end of the collection tube has an external thread and the aperture located at the front end of the specimen container has a mating internal thread.

(12) In a further variant, the collection tube further includes at least one lever to assist in attaching the collection tube to the aperture of the specimen container.

(13) In still a further variant, the one-way valve further includes a membrane formed of pliable material, the membrane has a central opening, and the opening is urged closed by an elastic nature of the membrane.

(14) In yet a further variant, the port tube is formed of resilient material, is rotatably attached at an opening in a side wall of the tubing of the urinary drainage system and further includes first and second sealing gaskets located adjacent the first end. The first sealing gasket is located upon an interior wall of the tubing and the second sealing gasket is located upon an exterior wall of the tubing.

(15) In a final variant of the invention, the port tube further includes a base portion. The base portion has a hollow core with an attachment end and a first fitting end. The base portion is attached at the attachment end at an opening in a side wall of the tubing of the urinary drainage system. Inner and outer sealing gaskets are located adjacent the attachment end. The inner sealing gasket is located upon an interior wall of the tubing. The outer sealing gasket is located upon an exterior wall of the tubing. A tube portion is provided. The tube portion has a hollow interior, a second fitting end and a valve end. The second fitting end of the tube portion is rotatably attached to the first fitting end of the base portion. The tube portion has a one-way valve located adjacent the valve end.

An appreciation of the other aims and objectives of the present invention and an understanding of it may be achieved by referring to the accompanying drawings and the detailed description of a preferred embodiment.

DESCRIPTION OF THE DRAWINGS

FIG. 1 is a side elevational view of the preferred embodiment of the invention attached to an indwelling catheter and urinary drainage system;

FIG. 2 is a perspective view of the FIG. 1 embodiment illustrating an internal one-way valve;

FIG. 4 is a cross-sectional view of the FIG. 1 embodiment and a perspective view of a specimen container, with attached collection tube and shaped nozzle and protective cover;

FIG. 5 is a partial perspective view of an alternative specimen container in which the piston for urine withdrawal has two seals;

FIG. 5A is a partial perspective view of an alternative specimen container in which the piston is attached to the actuating rod with a round connector on a single seal;

FIG. 5B is a partial perspective view of an alternative specimen container in which the piston for urine withdrawal has two seals and the piston is attached to the actuating rod with a threaded connector;

FIG. 6 is a partial perspective view of a threaded attachment to the collection tube to the specimen container;

DETAILED DESCRIPTION OF THE PREFERRED EMBODIMENT (1) FIGS. 1-8 illustrate a closed specimen collection system 10 providing the desired features that may be constructed from the following components. A port tube 14 is provided. The port tube 14 has a first end 18, a second end 22 and is rotatably attached at the first end 18 to tubing 20 of a urinary drainage system 26 attached to an indwelling urinary catheter 30. The port tube 14 has a one-way valve 34 located adjacent the second end 22. The second end 22 is formed to fit sealably with a shaped nozzle 38.

Figure 3:
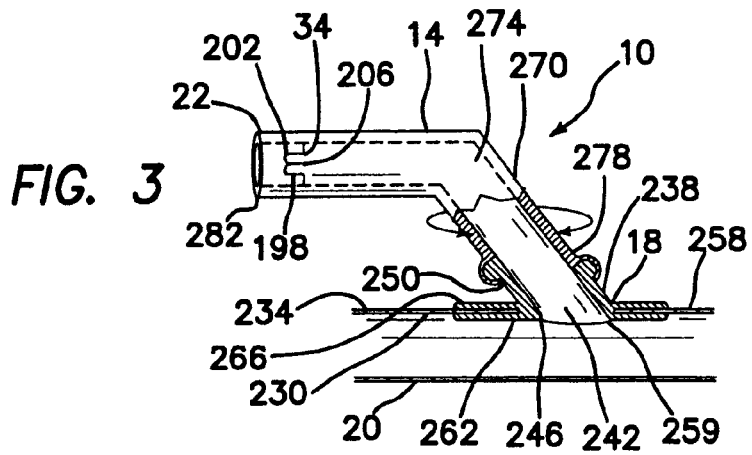
FIG. 3 is a side elevational view of a second embodiment providing an internal swivel feature.

(2) In a variant of the invention, as illustrated in FIG. 4, a collection tube 42 is provided. The collection tube 42 has a proximal end 46 and a distal end 50 and has a shaped nozzle 38 at the proximal end 46. The shaped nozzle 38 is adapted to fit sealably into the port tube 14 at the second end 22 adjacent the one-way valve 34. A protective cover 54 is provided. The cover 54 is attached to the collection tube 42 adjacent the proximal end 46, has a hollow interior 58 and extends a first predetermined distance 62 past an outer end 66 of the shaped nozzle 38.

A specimen container 70 is provided. The container 70 has a hollow body 74, a front end 78 and a back end 82. The front end 78 has an aperture 86. The aperture 86 is sized and shaped to attach to the distal end 50 of the collection tube 42. The aperture 86 is sealable after removal of the distal end 50 of the collection tube 42 there from. A piston 90 is provided. The piston 90 fits closely within the hollow body 74 and is attached to an actuating rod 94. When the port tube 14 is connected to the collection tube 42, the collection tube 42 is connected to the specimen container 70 and the actuating rod 94 is moved away from the front end 78 of the container 70, urine (not shown) will flow into the specimen container 70 in a sterile condition.

(3) In another variant, the collection tube 42 further includes a flexible portion 80 between the proximal end 46 and the distal end 50.

Figure 7:
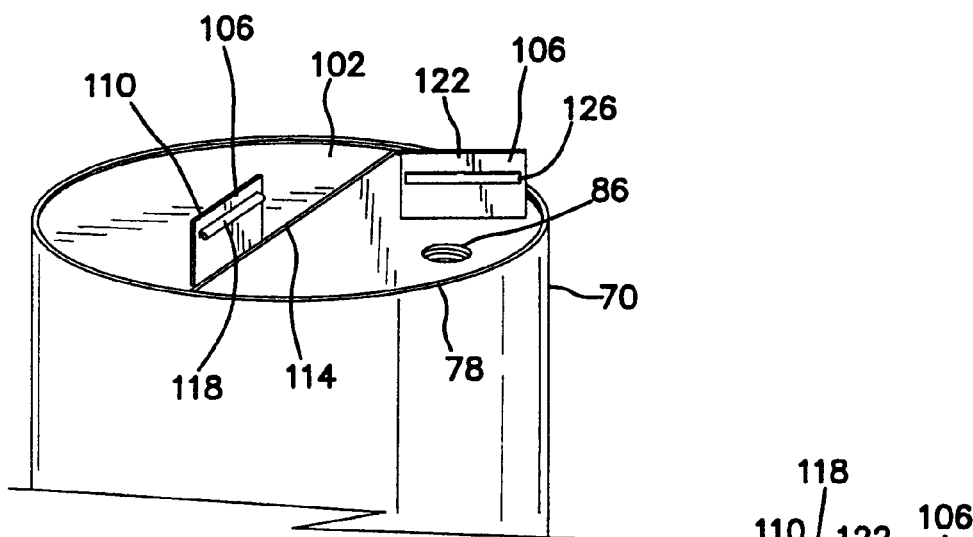
FIG. 7 is a partial perspective view of the specimen container illustrating a latching mechanism.

(4) In still another variant, as illustrated in FIGS. 4 and 7, the front end 78 of the specimen container 70 includes a rotating lid 102, the lid 102 sealably closing the aperture 86.

Figure 8:
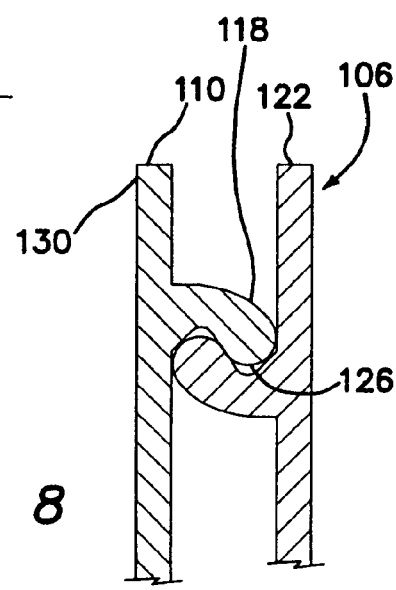
FIG. 8 is a cross-sectional side elevational view of a detail of the latching mechanism.

(5) In yet another variant, as illustrated in FIGS. 7 and 8, a latching mechanism 106 is provided. The latching mechanism 106 controls rotation of the lid 102.

(6) In a further variant, the latching mechanism 106 further includes a rotating portion 110. The rotating portion 110 is affixed to a leading edge 114 of the rotating lid 102 and has a projecting ledge 118 located parallel to the leading edge 114. A fixed portion 122 is provided. The fixed portion 122 is attached to the front end 78 of the specimen container 70 and has a receiving slot 126 sized, shaped and located to mate frictionally with the projecting ledge 118. When the rotating lid 102 is positioned to seal the aperture 86, the projecting ledge 118 will be secured within the receiving slot 126.

(7) In still a further variant, the latching mechanism 106 further includes a retracting tab 130 attached to the rotating portion 110, the retracting tab 130 assisting in opening the aperture 86.

(8) In yet a further variant, as illustrated in FIGS. 4 and 5A, the piston 90 further includes a seal 134. The seal 134 has a front side 138 and a back side 142 and is sized and shaped to fit closely within the hollow body 74. The seal 134 is located adjacent the front end 78 of the specimen container 70. The seal 134 has a central receiving port 146 located at its center portion 150. A first end 154 of the actuating rod 94 is sized and shaped to removably engage the central receiving port 146. When the actuating rod 94 has withdrawn the piston 90 toward the back end 82 of the specimen container 70, the actuating rod 94 is removed from the receiving port 146, the aperture 86 is sealed and the specimen container 70 will contain a sterile urine sample.

(9) In another variant of the invention, as illustrated in FIGS. 5 and 5B, the piston 90 further includes a first seal 158. The first seal 158 has a front side 162 and a back side 166 and is sized and shaped to fit closely within the hollow body 74. The first seal 158 is located adjacent the front end 78 of the specimen container 70. A second seal 170 is provided. The second seal 170 is sized and shaped to fit closely within the hollow body 74 and has a central receiving port 146 located at a center portion 150 of the second seal 170. The second seal 170 is spaced from the back side 166 of the first seal 158 and attached thereto at an outer surface 174 of the receiving port 146. A first end 154 of the actuating rod 94 is sized and shaped to removably engage the central receiving port 146. When the actuating rod 94 has withdrawn the piston 90 toward the back end 82 of the specimen container 70, the actuating rod 94 is removed from the receiving port 146, the aperture 86 is sealed and the specimen container 70 will contain a sterile urine sample 98.

(10) In still another variant, as illustrated in FIG. 5B, the actuating rod 94 has a male thread 178 at the first end 154 and the central receiving port 146 has a mating female thread 182.

(11) In yet another variant, as illustrated in FIG. 6, the distal end 50 of the collection tube 42 has an external thread 186 and the aperture 86 located at the front end 78 of the specimen container 70 has a mating internal thread 190.

(12) In a further variant, the collection tube 42 further includes at least one lever 194 to assist in attaching the collection tube 42 to the aperture 86 of the specimen container 70.

(13) In still a further variant, as illustrated in FIGS. 1-4, the one-way valve 34 further includes a membrane 198 formed of pliable material 202, the membrane 198 has a central opening 206, and the opening 206 is urged closed by an elastic nature of the membrane 198.

(14) In yet a further variant, as illustrated in FIG. 1, the port tube 14 is formed of resilient material 210, is rotatably attached at an opening 214 in a side wall 218 of the tubing 20 of the urinary drainage system 26 and further includes first 222 and second 226 sealing gaskets located adjacent the first end 18. The first sealing gasket 222 is located upon an interior wall 230 of the tubing 20 and the second sealing gasket 226 is located upon an exterior wall 234 of the tubing 20.

(15) In another variant of the invention, as illustrated in FIG. 3, the port tube 14 further includes a base portion 238. The base portion 238 has a hollow core 242 with an attachment end 246 and a first fitting end 250. The base portion 238 is attached at the attachment end 246 at an opening 254 in a side wall 258 of the tubing 20 of the urinary drainage system 26. Inner 262 and outer 266 sealing gaskets are located adjacent the attachment end 246. The inner sealing gasket 262 is located upon an interior wall 230 of the tubing 20. The outer sealing gasket 266 is located upon an exterior wall 234 of the tubing 20. A tube portion 270 is provided. The tube portion 270 has a hollow interior 274, a second fitting end 278 and a valve end 282. The second fitting end 278 of the tube portion 270 is rotatably attached to the first fitting end 250 of the base portion 238. The tube portion 270 has a one-way valve 34 located adjacent the valve end 282.

The closed specimen collection system 10 has been described with reference to particular embodiments. Other modifications and enhancements can be made without departing from the spirit and scope of the claims that follow.

The invention claimed is:

1. A closed specimen collection system, comprising: a port tube, said port tube having a first end and a second end said first end being offset at an angle from said second end and being pivotably attached at said first end directly to a side wall of tubing of a urinary drainage system attached to an indwelling urinary catheter; said port tube having a one-way valve disposed in said port tube adjacent said second end; said second end being formed to fit sealably with a shaped nozzle.

2. The closed specimen collection system, as described in claim 1, further comprising:
   a collection tube, said collection tube having a proximal end and a distal end and having a shaped nozzle at said proximal end;
   said shaped nozzle being adapted to fit sealably into said port tube at said second end adjacent said one-way valve;
   a protective cover, said cover being fixedly attached to said collection tube adjacent said proximal end, having a hollow interior and extending a first predetermined distance past an outer end of said shaped nozzle;
   a specimen container, said container having a hollow body, a front end and a back end;
   said front end having an aperture, said aperture being sized and shaped to removably attach to said distal end of said collection tube;
   an integral rotating lid, said rotating lid sealing said aperture after removal of said distal end of said collection tube;
   a piston, said piston fitting closely within said hollow body and being attached to an actuating rod; and
   whereby, when said port tube is connected to said collection tube, said collection tube is connected to said specimen container and said actuating rod is moved away from said front end of said container, urine will flow into said specimen container in a sterile condition.

3. The closed specimen collection system, as described in claim 2, wherein said collection tube further comprises a flexible portion between said proximal end and said distal end.

4. The closed specimen collection system, as described in claim 2, wherein said front end of said specimen container includes a rotating lid, said lid rotating to sealably close said aperture.

5. The closed specimen collection system, as described in claim 4, further comprising a latching mechanism, said latching mechanism controlling rotation of said lid.

6. The closed specimen collection system, as described in claim 5, wherein said latching mechanism further comprises:
   a rotating portion, said rotating portion affixed to a leading edge of said rotating lid, said rotating lid rotating to seal said aperture, and having a projecting ledge disposed parallel to said leading edge;
   a fixed portion, said fixed portion affixed to said front end of said specimen container, having a receiving slot sized, shaped and disposed to mate frictionally with said projecting ledge; and
   whereby, when said rotating lid is positioned to seal said aperture, said projecting ledge will be secured within said receiving slot.

7. The closed specimen collection system, as described in claim 6, wherein said latching mechanism further comprises a retracting tab attached to said rotating portion, said retracting tab assisting in opening said aperture.

8. The closed specimen collection system, as described in claim 2, wherein said piston further comprises:
   a seal, said seal having a front side and a back side and being sized and shaped to fit closely within said hollow body and disposed adjacent said front end of said specimen container;
   said seal, having a central receiving port disposed at a center portion thereof;
   a first end of said actuating rod be sized and shaped to removably engage said central receiving port; and
   whereby, when said actuating rod has withdrawn said piston toward said back end of said specimen container, said actuating rod is removed from said receiving port and when said aperture is sealed said specimen container will contain a sterile urine sample.

9. The closed specimen collection system, as described in claim 2, wherein said piston further comprises:
   a first seal, said first seal having a front side and a back side and being sized and shaped to fit closely within said hollow body and disposed adjacent said front end of said specimen container;
   a second seal, said second seal being sized and shaped to fit closely within said hollow body and having a central receiving port penetrating a center portion of said second seal;
   said second seal being spaced from said back side of said first seal and attached thereto at an outer surface of said receiving port;
   a first end of said actuating rod be sized and shaped to removably engage said central receiving port; and
   whereby, when said actuating rod has withdrawn said piston toward said back end of said specimen container, said actuating rod is removed from said receiving port, said aperture is sealed and said specimen container will contain a sterile urine sample.

10. The closed specimen collection system, as described in claim 8, wherein said actuating rod has a male thread at said first end and said central receiving port has a mating female thread.

11. The closed specimen collection system, as described in claim 2, wherein said distal end of said collection tube has an external thread and said aperture disposed at said front end of said specimen container has a mating internal thread.

12. The closed specimen collection system, as described in claim 2, wherein said collection tube further comprises at least one lever to assist in attaching said collection tube to said aperture of said specimen container.

13. The closed specimen collection system, as described in claim 1, wherein said one-way valve further comprises a membrane formed of pliable material, said membrane having a central opening, said opening being urged closed by an elastic nature of said membrane.

14. The closed specimen collection system, as described in claim 1, wherein said port tube is formed of resilient material, is rotatably attached at an opening in a side wall of said tubing of said urinary drainage system and further comprises:
   first and second sealing gaskets disposed adjacent said first end;
   said first sealing gasket disposed upon an interior wall of said tubing; and
   said second sealing gasket disposed upon an exterior wall of said tubing.

15. The closed specimen collection system, as described in claim 1, wherein said port tube further comprises:
- a base portion, said base portion having a hollow core with an attachment end and a first fitting end and being attached at said attachment end at an opening in a side wall of said tubing of said urinary drainage system;
- inner and outer sealing gaskets disposed adjacent said attachment end:
- said inner sealing gasket disposed upon an interior wall of said tubing;
- said outer sealing gasket disposed upon an exterior wall of said tubing;
- a tube portion, said tube portion having a hollow interior, a second fitting end and a valve end;
- said second fitting end of said tube portion being rotatably attached to said first fitting end of said base portion; and
- said tube portion having a one-way valve disposed adjacent said valve end.

* * * * *